United States Patent
Armstrong-Ostle et al.

(10) Patent No.: US 9,168,186 B2
(45) Date of Patent: Oct. 27, 2015

(54) ABSORBENT CORE HAVING VARIED BASIS WEIGHT OF ABSORBENT MATERIAL AND ADHESIVE

(75) Inventors: Peter Armstrong-Ostle, Euskircken (DE); Harald Hundorf, Euskircken (DE); Brigit Wirtz, Euskircken (DE); Torsten Frings, Euskircken (DE); Bruno Johannes Ehrnsperger, Schwalbach (DE); Maike Thomann, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 506 days.

(21) Appl. No.: 13/491,960

(22) Filed: Jun. 8, 2012

(65) Prior Publication Data

US 2012/0316530 A1     Dec. 13, 2012

(30) Foreign Application Priority Data

Jun. 10, 2011   (EP) .................................. 11004768

(51) Int. Cl.
  *A61F 13/15*   (2006.01)
  *A61F 13/20*   (2006.01)
  *A61F 13/532*  (2006.01)
  *A61F 13/539*  (2006.01)

(52) U.S. Cl.
  CPC .............. *A61F 13/532* (2013.01); *A61F 13/539* (2013.01)

(58) Field of Classification Search
  CPC ............................ A61F 13/532; A61F 13/539
  USPC ....................................................... 604/366
  See application file for complete search history.

(56) References Cited

U.S. PATENT DOCUMENTS

| | | | |
|---|---|---|---|
| 2003/0119402 A1 | 6/2003 | Melius et al. | |
| 2006/0009743 A1 | 1/2006 | Wang et al. | |
| 2007/0093164 A1* | 4/2007 | Nakaoka | 442/385 |
| 2010/0004614 A1 | 1/2010 | Ashton et al. | |

FOREIGN PATENT DOCUMENTS

| GB | 1566594 | 5/1980 |
|---|---|---|
| JP | 10-337305 | 12/1998 |

OTHER PUBLICATIONS

International Search Report, PCT/US2012/041498, mailed Jul. 26, 2012, 10 pages.

* cited by examiner

*Primary Examiner* — Melanie Hand
*Assistant Examiner* — Aundria Hairell
(74) *Attorney, Agent, or Firm* — Wednesday G. Shipp; Andrew A Paul; Richard L. Alexander

(57) ABSTRACT

An absorbent core comprising a substrate layer and an absorbent layer, the absorbent layer comprising an absorbent material and a thermoplastic adhesive material; the absorbent core has longitudinal and transverse dimensions and consists of nine transverse segments in its longitudinal dimension and six longitudinal segments in its transverse dimension; in each of the transverse segments and longitudinal segments, the absorbent layer has average basis weights of absorbent material of thermoplastic adhesive material; the basis weights of the absorbent layer in at least one of the transverse segments are lower than the basis weights of the absorbent layer in at least one other of the transverse segments; and the basis weights of the absorbent layer in at least one of the longitudinal segments are lower than the basis weights of the absorbent layer in at least one other of the longitudinal segments.

14 Claims, 10 Drawing Sheets

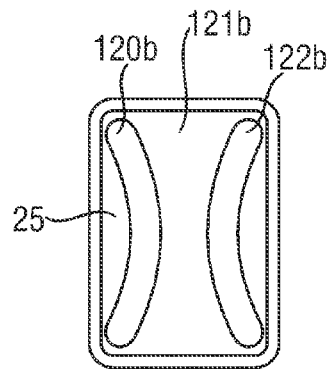
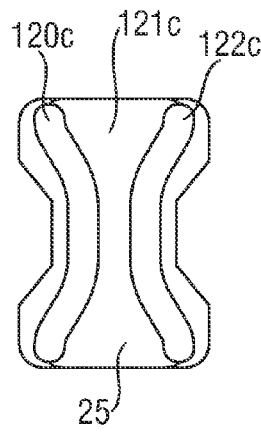
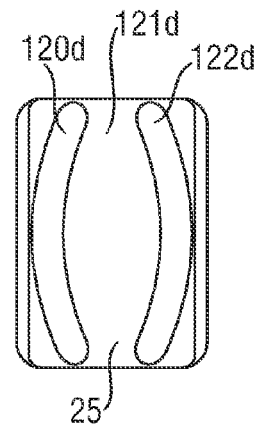
Fig. 6A          Fig. 6B          Fig. 6C
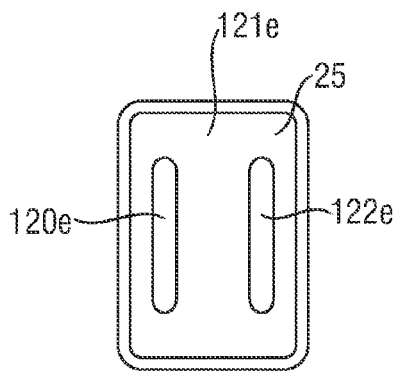
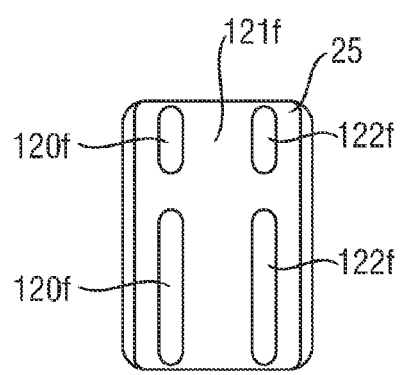
Fig. 6D          Fig. 6E

ABSORBENT CORE HAVING VARIED BASIS WEIGHT OF ABSORBENT MATERIAL AND ADHESIVE

CROSS REFERENCE TO RELATED APPLICATION

This application claims priority to European Patent Convention Application 11004768.5, filed Jun. 10, 2011, the substance of which are incorporated herein by reference.

FIELD OF THE INVENTION

The present disclosure generally relates to absorbent core for disposable absorbent articles.

BACKGROUND OF THE INVENTION

Absorbent articles, such as disposable diapers, training pants, and adult incontinence undergarments, absorb and contain body exudates. They are also intended to prevent body exudates from soiling, wetting, or otherwise contaminating clothing or other articles, such as, bedding, that come in contact with the wearer. A disposable absorbent article, such as a disposal diaper, may be worn for several hours in a dry state or in a urine loaded state. Accordingly, efforts have been made toward improving the fit and comfort of the absorbent article to the wearer, both when the article is dry and when the article is fully or partially loaded with liquid exudates, while maintaining or enhancing the absorbing and containing functions of the article.

An important component of disposable absorbent articles is the absorbent core structure. Absorbent core structures typically include absorbent polymer material and cellulose fibers. The absorbent polymer material ensures that large amounts of bodily fluids, e.g. urine, can be absorbed by the absorbent article during its use and be locked away, thus providing low rewet and good skin dryness. The absorbent core structure is typically profiled, i.e. provided with regions of different capacity.

Some disposable absorbent articles, like disposable diapers, have been made thinner by reducing or eliminating these cellulose fibres from the absorbent core structure. To maintain the mechanical stability of the absorbent core structures, small quantities of adhesive material, such as thermoplastic adhesive materials, are added to stabilize the absorbent polymer material. Resultantly, absorbent structures having the required permeability/porosity, reduced gel-blocking, and that form stable structures in use or transport are provided.

However, it was found that some of these profiled absorbent core structures with reduced cellulose fibre content may not always provide satisfactory acquisition speed.

Therefore, there is still a need to provide absorbent core for disposable absorbent articles which are thin and deliver good fluid handling performances.

SUMMARY OF THE INVENTION

The invention relates to an absorbent core for disposable absorbent articles comprising one or more absorbent structures. The absorbent structure comprises a substrate layer and an absorbent layer. The absorbent layer comprises an absorbent material supported by, and immobilized on said substrate layer by a thermoplastic adhesive material. The absorbent core has a longitudinal dimension and a transverse dimension and consists of nine transverse segments in its longitudinal dimension and of six longitudinal segments in its transverse dimension. In each of said transverse segments, the absorbent layer has an average basis weight of absorbent material ($APM_t\ BW_{av}$) and an average basis weight of thermoplastic adhesive material ($TAM_t\ BW_{av}$) immobilizing said absorbent material. In each of said longitudinal segments, the absorbent layer has an average basis weight of absorbent material ($APM_1\ BW_{av}$) and an average basis weight of thermoplastic adhesive material ($TAM_1\ BW_{av}$) immobilizing said absorbent material. The $APM_t\ BW_{av}$ and $TAM_t\ BW_{av}$ of the absorbent layer in at least one of the transverse segments of the absorbent core are lower relative to the $APM_t\ BW_{av}$ and $TAM_t\ BW_{av}$ of the absorbent layer in at least one other of the transverse segments. Alternatively, the $APM_1\ BW_{av}$ and $TAM_1\ BW_{av}$ in at least one of the longitudinal segments are lower relative to the $APM_1\ BW_{av}$ and $TAM_1\ BW_{av}$ in at least one other longitudinal segments.

BRIEF DESCRIPTION OF THE DRAWINGS

FIGS. 6A to 6E are top views of an absorbent core showing the absorbent layer profiling.

DETAILED DESCRIPTION OF THE INVENTION

Definitions

Figure 1:
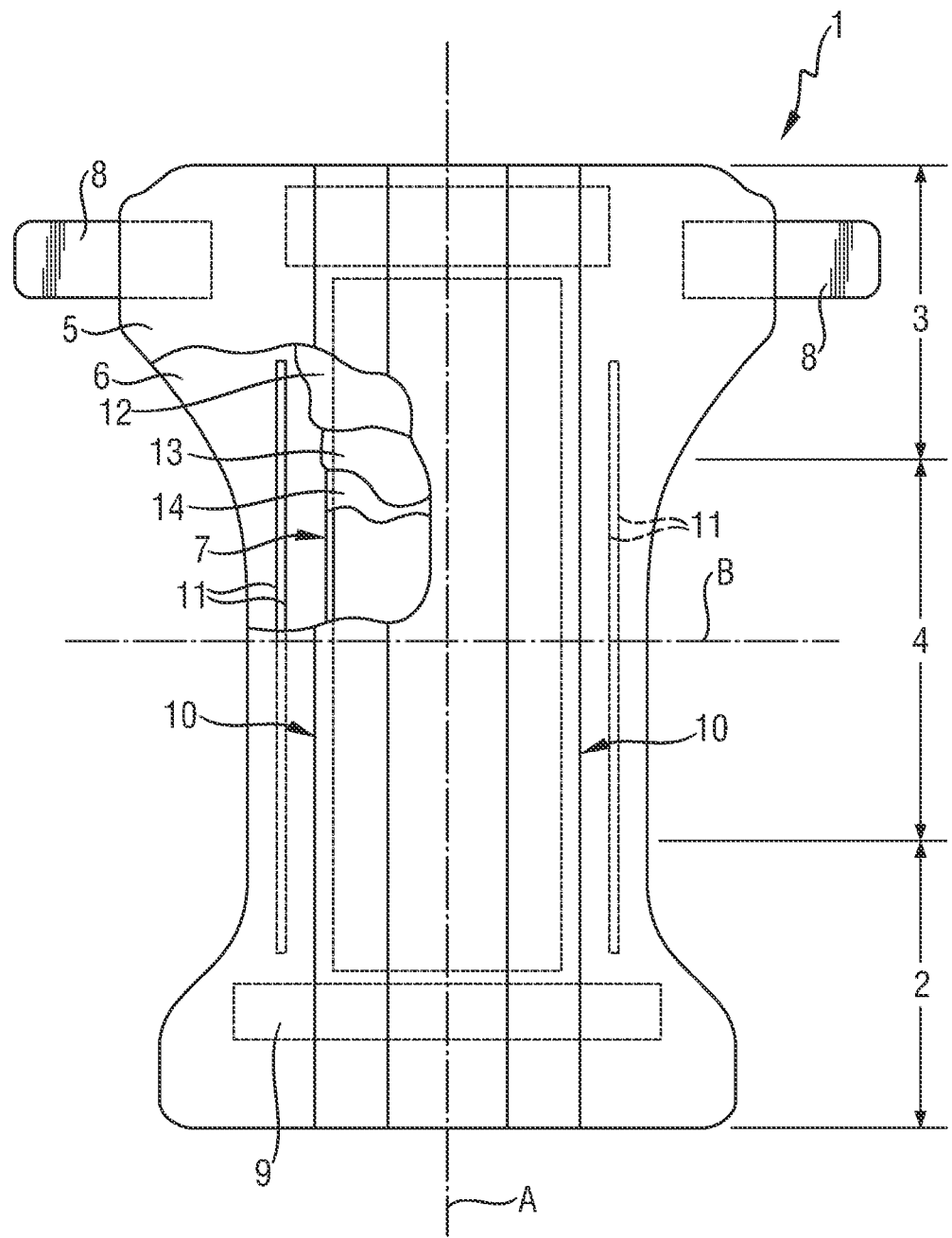
FIG. 1 is a plan view of a disposable diaper.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products.

"Diapers" refers to devices generally worn by infants and incontinent persons about the lower torso so as to encircle the waist and legs of the wearer. Examples of diapers include infant or adult diapers and pant-like diapers such as training pants.

"Training pant" refers to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

"Disposable" is used herein to describe articles that are generally not intended to be laundered or otherwise restored or reused (i.e., they are intended to be discarded after a single use and, may be recycled, composted or otherwise disposed of in an environmentally compatible manner).

"Absorbent core" refers to a structure typically disposed between a topsheet and backsheet of an absorbent article for absorbing and containing liquid received by the absorbent article. The absorbent core may comprise one or more substrate layer, absorbent material disposed on the one or more substrate layer, and a thermoplastic adhesive composition on the absorbent material. The thermoplastic adhesive composition may be on the absorbent material and at least a portion of the one or more substrate layer. The absorbent core does not include an acquisition system, a topsheet, or a backsheet of the absorbent article. In a certain embodiment, the absorbent core would consist essentially of the one or more substrate layers, the absorbent material, the thermoplastic adhesive composition, and optionally the cover layer.

"Absorbent polymer material" refers to cross linked polymeric materials that can absorb at least 10 times their weight of an aqueous 0.9% saline solution as measured using the Centrifuge Retention Capacity test (Edana 441.2-01).

"Absorbent polymer particles" is used herein to refer to an absorbent polymer material which is in particulate form so as to be flowable in the dry state.

"Nonwoven material" refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which may comprise spunlaying, meltblowing, carding, airlaying, wetlaying, coform and combinations thereof. The fibers may be of natural or man-made origin and may be staple fibers or continuous filaments or be formed in situ.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present disclosure forms a fibrous network over the absorbent material.

Disposable Absorbent Articles

The disposable absorbent article is a device that absorbs and contains body exudates. It may include diapers, training pants, adult incontinence undergarments, feminine hygiene products. Typically, the disposable article comprises a topsheet, a backsheet and an absorbent core in-between.

An exemplary embodiment of a disposable absorbent article is disposable diaper such as illustrated in FIG. 1.

The disposable diaper 1, such as illustrated in FIG. 1, has a longitudinal dimension (along a longitudinal axis A) and a transverse dimension (along a transverse axis B) perpendicular thereto.

One end portion of the diaper is configured as a front waist region 2 (which is the front one third of the article, having one third of the length of the article). The opposite end portion is configured as a back waist region 3 (which is the back one third of the article, having one third of the length of the article). An intermediate portion of the diaper is configured as a crotch region 4 (which is the centre one third of the article). The crotch region extends longitudinally between the front and back waist regions. The crotch region is that portion of the diaper which, when the diaper is worn, is generally positioned between the wearer's legs.

The diaper typically comprises a topsheet 5, a backsheet 6 and an absorbent core 7 disposed therebetween.

The topsheet may be liquid pervious. The topsheet may be at least partially hydrophilic. So-called apertured topsheets may also be used. Topsheets with one or more (large) openings may also be used. The topsheet may also include a skin care composition, e.g., a lotion. The topsheet may be fully or partially elasticized or may be foreshortened to provide a void space between the topsheet and the absorbent core. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet may be vapor pervious but liquid impervious. The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. In certain embodiments, the backsheet may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind and sold under the trade names X15306, X10962, and X10964. Other suitable backsheet materials may include breathable materials that permit vapors to escape from the diaper while still preventing liquid exudates from passing through the backsheet. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

The diaper may further comprise a front and back waist band and/or a fastening system, typically joined to the waistband, as known in the art. Preferred fastening systems comprise fastening tabs 8 and landing zones 9, wherein the fastening tabs are attached or joined to the back waist region of the diaper and the landing zones are part of the front waist region of the diaper. The diaper may also have leg cuffs 10 and/or barrier cuffs, such as elasticized barrier cuffs 11. Suitable cuffs are described, for example, in U.S. Pat. Nos. 3,860, 003; 4,808,178 and 4,909; 4,695,278 and 4,795,454.

As illustrated in FIG. 1, an acquisition system comprising an upper acquisition layer 12 and a lower acquisition layer 13 and optionally a core cover 14 may be disposed on the absorbent core. The acquisition system may serve as a temporary reservoir for liquid until the absorbent structure can absorb the liquid. In a certain embodiment, the acquisition system may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. According to certain embodiments, the cross-linked cellulosic fibers may be crimped, twisted, or curled, or a combination thereof including crimped, twisted, and curled. In a certain embodiment, one or both of the upper and lower acquisition layers may comprise a non-woven, which may be hydrophilic. Further, according to a certain embodiment, one or both of the upper and lower acquisition layers may comprise the chemically cross-linked cellulosic fibers, which may or may not form part of a nonwoven material. According to an exemplary embodiment, the upper acquisition layer may comprise a nonwoven, without the cross-linked cellulosic fibers, and the lower acquisition layer may comprise the chemically cross-linked cellulosic fibers. Further, according to an embodiment, the lower acquisition layer may comprise the chemically cross-linked cellulosic fibers mixed with other fibers such as natural or synthetic polymeric fibers. Suitable non-woven materials for the upper and lower acquisition layers include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

Processes for assembling the diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. While the topsheet, the backsheet, and the absorbent core may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

Absorbent Core.

The absorbent core is disposed between the topsheet and the backsheet. It is a three-dimensional structure which comprises at least one absorbent structure.

An absorbent structure comprises a substrate layer and an absorbent layer supported by, and immobilized on said substrate layer by a thermoplastic adhesive material.

The absorbent layer comprises an absorbent polymer material and optionally cellulose fibers.

Figure 2:
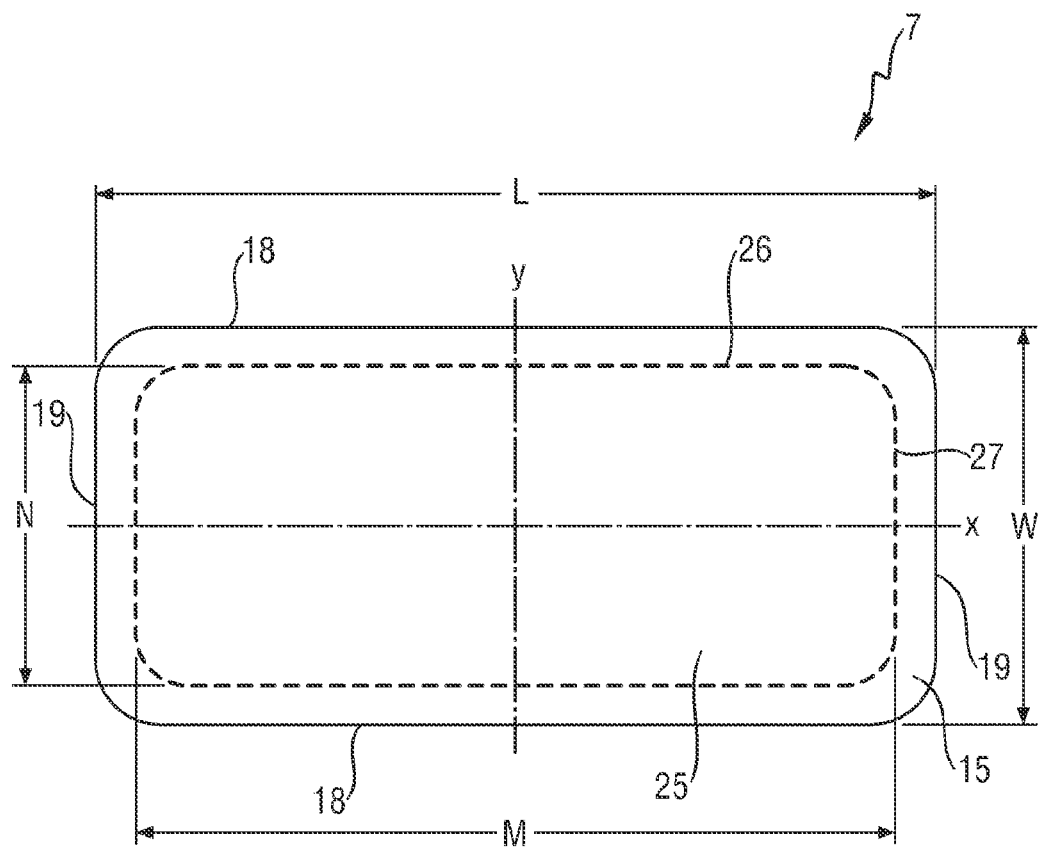
FIG. 2 is a top view of an absorbent core.

The absorbent core 7, as shown in FIG. 2, has a longitudinal dimension L (i.e. a length L) extending in the longitudinal dimension of the diaper and a transverse dimension W (i.e. a width W) extending in the transverse dimension of the diaper. The absorbent core 7 comprises a substrate layer 15 and an absorbent layer 25 supported by, and immobilized on said substrate layer by a thermoplastic adhesive material.

The absorbent core possesses a central longitudinal axis x, a central transverse axis y perpendicular to said central longitudinal axis x, a pair of opposing longitudinal edges 18 extending in the longitudinal dimension of the disposable diaper and a pair of opposing transverse edges 19 extending in the transverse dimension of the disposable diaper. The longitudinal edges or transverse edges of the absorbent core may be parallel respectively to the central longitudinal axis or central transverse axis or they may follow the general direction of these axes while not being strictly parallel, e.g. they may be curvilinear and for instance provide for a narrower transverse dimension in the crotch region.

The absorbent core has a front region (which is the region oriented toward the front waist region of the disposable diaper) which makes up one third of the longitudinal dimension L of the absorbent core. The opposite end region is configured as a back region (which is the region oriented toward the back waist region of the diaper) which makes up one third of the longitudinal dimension L of the absorbent core. An intermediate portion of the absorbent core is configured as a crotch region which makes up one third of the longitudinal dimension L of the absorbent core. The front, crotch and back regions are arranged sequentially in the longitudinal dimension of the absorbent core.

Figure 3:
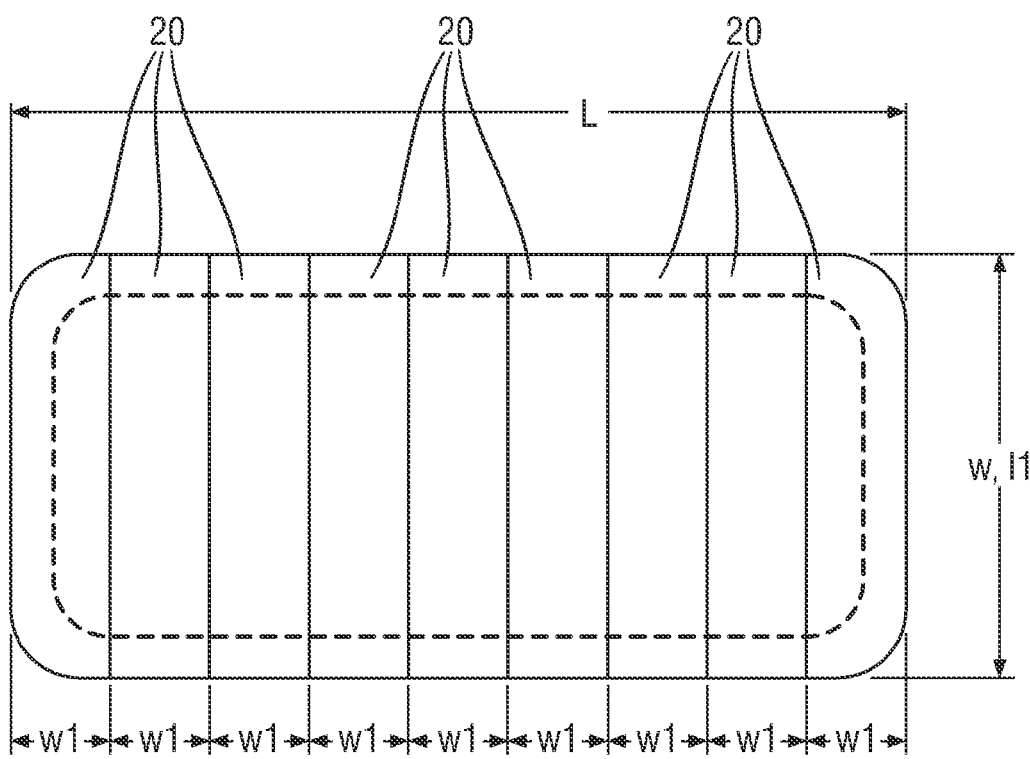
FIG. 3 is a top view of an absorbent core showing the transverse segments.

The absorbent core may be, for the purpose of the present disclosure, as shown in FIG. 3, virtually divided in nine segments in its longitudinal dimension, these segments being referred herein individually as transverse segments 20. The transverse segments extend from one longitudinal edge of the absorbent core to the other through the thickness of the absorbent core. They have a length $l_1$ which is equal to the width W of the absorbent core and a width $w_1$ which correspond to ⅑ of the length L of the absorbent core. In some embodiments, the transverse segments may have a length of at least 4 cm, or at least 5 cm, or at least 7 cm or at least 8 cm, or at least 9 cm and a width of at least 1.5 cm, at least 2.5 cm, or at least 3 cm or at least 3.8 cm or at least 4 cm.

Each transverse segment comprises an absorbent layer which has an average basis weight of absorbent material, referred herein as $APM_t\ BW_{av}$ and an average basis weight of thermoplastic adhesive material, referred herein as $TAM_t\ BW_{av}$.

The $APM_t\ BW_{av}$ is the average weight of absorbent material per surface area of the absorbent layer comprised by a transverse segment when the absorbent core comprises only one absorbent structure and therefore only one absorbent layer, $APM_t\ BW_{av}$ is typically expressed in gram per square meter. The average weight is calculated by determining the weight of absorbent material in the absorbent layer comprised in a segment and divided it by the total surface area of the absorbent layer in said segment. When the absorbent material consists of absorbent polymer material, the $APM_t\ BW_{av}$ is the average weight of absorbent polymer material per surface area of the absorbent layer comprised by said transverse segment. When the absorbent core comprises two or more absorbent structures forming a laminate, the $APM_t\ BW_{av}$ is the average weight of absorbent material per surface area of the laminate comprised by said transverse segment (i.e. the average weight of absorbent material for the combined absorbent layers in the segment).

The $TAM_t\ BW_{av}$ is the average weight of thermoplastic adhesive material per surface area of the absorbent layer comprised by the transverse segment when the absorbent core comprises only one absorbent structure and therefore only one absorbent layer. The $TAM_t\ BW_{av}$ is typically expressed in gram per square meter. The average weight is calculated by determining the weight of thermoplastic adhesive material in the absorbent layer comprised in a segment and divided it by the total surface area of the absorbent layer in said segment. When the absorbent core comprises two or more absorbent structures forming a laminate, the $TAM_t\ BW_{av}$ is the average weight of thermoplastic adhesive material per surface area of the laminate comprised by said transverse segment.

Figure 4:
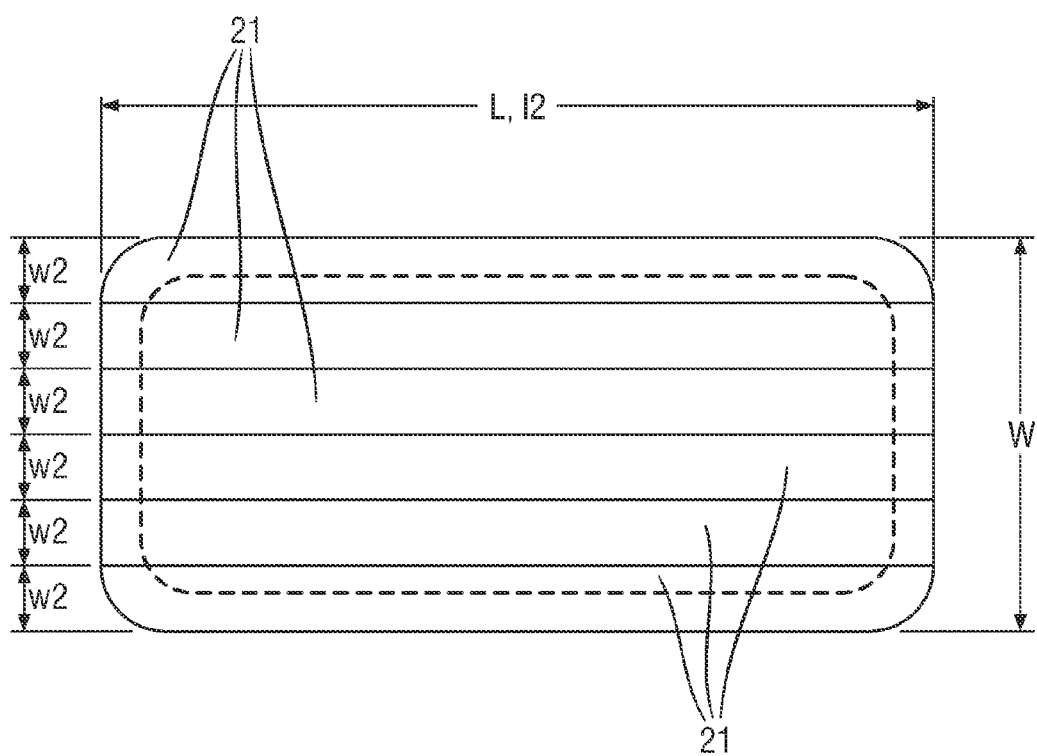
FIG. 4 is a top view of an absorbent core showing the longitudinal segments.

As shown in FIG. 4, the absorbent core may be, for the purpose of the present disclosure, virtually divided in six segments 21 in its transverse dimension, these segments being referred herein individually as longitudinal segments. The longitudinal segments extend from one transverse edge of the absorbent core to the other through the thickness of the absorbent core. They have a length $l_2$ which is equal to the length L of the absorbent core and a width $w_2$ which correspond to ⅙ of the width W of the absorbent core.

Each longitudinal segment comprises an absorbent layer which has an average basis weight of absorbent material, referred herein as $APM_1\ BW_{av}$ and an average basis weight of thermoplastic adhesive material, referred herein as $TAM_1\ BW_{av}$.

The $APM_1\ BW_{av}$ is the average weight of absorbent material per surface area of the absorbent layer comprised by one longitudinal segment when the absorbent core comprises only one absorbent structure and therefore only one absorbent layer. The $APM_1\ BW_{av}$ is typically expressed in gram per square meter. The average weight is calculated by determining the weight of absorbent material in the absorbent layer comprised in a segment and divided it by the total surface area of the absorbent layer in said segment. When the absorbent material consists of absorbent polymer material, the $APM_1\ BW_{av}$ is the average weight of absorbent polymer material per surface area of the absorbent layer comprised by said longitudinal segment. When the absorbent core comprises two or more absorbent structures forming a laminate, the $APM_1\ BW_{av}$ is the average weight of absorbent material per surface area of the laminate comprised by said longitudinal segment (i.e. the average weight of absorbent material for the combined absorbent layers in the segment).

The $TAM_1\ BW_{av}$ is the average weight of thermoplastic adhesive material per surface area of the absorbent layer comprised by said longitudinal segment when the absorbent core comprises only one absorbent structure and therefore only one absorbent layer, typically expressed in gram per square meter. The average weight is calculated by determining the weight of thermoplastic adhesive material in the absorbent layer comprised in a segment and divided it by the total surface area of the absorbent layer in said segment. When the absorbent core comprises two or more absorbent structures forming a laminate, the $TAM_1\ BW_{av}$ is the average weight of thermoplastic adhesive material per surface area of the laminate comprised by said longitudinal segment. When the absorbent core comprises two or more absorbent structures forming a laminate, the $TAM_1\ BW_{av}$ is the average weight of thermoplastic adhesive material per surface area of the laminate comprised by said longitudinal segment (i.e. the average weight of absorbent material for the combined absorbent layers in the segment).

Profiled Absorbent Core

The absorbent core is provided with regions of different absorbency, i.e. certain regions of the absorbent core comprise more absorbent material than other regions. In some embodiments, the absorbent core may be profiled in its longitudinal dimension, i.e. the amount of absorbent material, e.g. the amount of absorbent polymer material, in the absorbent layer or in at least one of the absorbent layers or in all the absorbent layers may vary in the longitudinal dimension of the absorbent core. In some other embodiments, the absorbent core may be profiled in its transverse dimension, i.e. the amount of absorbent material, e.g. the amount of absorbent polymer material, in the absorbent layer or in at least one of the absorbent layers or in all the absorbent layers may vary in the transverse dimension of the absorbent core. The amount of absorbent material, such as the amount of absorbent polymer material, may gradually transition from one region to another. This gradual transition in amount of absorbent material may reduce the possibility of cracks forming in the absorbent core.

As shown in FIG. 2, the absorbent layer has a longitudinal dimension M extending in the longitudinal dimension of the absorbent core (i.e. the absorbent layer has a length M) and a transverse dimension N extending in the transverse dimension of the absorbent core (i.e. the absorbent layer has a width N). The absorbent layer 25 possesses a central longitudinal axis x, a central transverse axis y perpendicular to said central longitudinal axis x, a pair of opposing longitudinal edges 26 extending in the longitudinal dimension of the absorbent core and a pair of opposing transverse edges 27 extending in the transverse dimension of the absorbent core. The longitudinal edges or transverse edges of the absorbent layer may be parallel respectively to the central longitudinal axis or central transverse axis or they may follow the general direction of these axes while not being strictly parallel, e.g. they may be curvilinear as for instance to provide for a narrower transverse dimension in the crotch region.

The absorbent layer comprises an absorbent material, typically an absorbent polymer material, and optionally cellulose fibers. The absorbent polymer material is typically in the form of particles, i.e. absorbent polymer particles. "Cellulose fibers" as used herein refers to comminuted wood pulp in the form of fibers, typically also referred in the art as "air-felt". In some embodiments, the absorbent material comprises more than 70%, or more than 80%, or more than 90%, or more than 95%, or even 100% by weight of absorbent polymer particles. In some embodiments, the absorbent material comprises absorbent polymer particles and less than 5% by weight of cellulose, more typically less than 2% by weight of cellulose and most typically the absorbent material is cellulose free. In embodiments wherein the absorbent layer is cellulose free, the absorbent layer comprises only absorbent polymer particles.

Typically the absorbent polymer particles suitable for use in the absorbent layer can comprise any absorbent polymer particles known from superabsorbent literature, for example such as described in Modern Superabsorbent Polymer Technology, F. L. Buchholz, A. T. Graham, Wiley 1998.

The absorbent polymer particles may be spherical, spherical-like or irregular shaped particles, such as Vienna-sausage shaped particles, or ellipsoid shaped particles of the kind typically obtained from inverse phase suspension polymerizations. The particles can also be optionally agglomerated at least to some extent to form larger irregular particles.

The absorbent polymer particles can be selected among polyacrylates and polyacrylate based materials that are internally and/or surface cross-linked, such as for example partially neutralized cross-linked polyacrylates or acid polyacrylate. Examples of absorbent polymer particles suitable in the present disclosure are described for instance in the PCT Patent Application WO 07/047,598, WO 07/046,052, WO2009/155265 and WO2009/155264.

The absorbent polymer particles may be internally cross-linked, i.e. the polymerization is carried out in the presence of compounds having two or more polymerizable groups which can be free-radically copolymerized into the polymer network. Useful crosslinkers include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962 as well as cross-linkers described in WO2009/155265.

The absorbent polymer particles may be externally cross-linked (post cross-linked). Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP-A 1 199 327 and morpholine-2,3-dione and its derivatives as described in WO 03/031482.

The absorbent polymer particles may have surface modifications, such as being coated or partially coated with a coating agent. Examples of coated absorbent polymer particles are disclosed in WO2009/155265. The coating agent may be such that it renders the absorbent polymer particles more hydrophilic. The coating agent may be a polymer, such as an elastic polymer or a film-forming polymer or an elastic film-forming polymer, which forms an elastomeric (elastic) film coating on the particle. The coating may be a homogeneous and/or uniform coating on the surface of the absorbent polymer particles. The coating agent may be applied at a level of from 0.1% to 5%, or from 0.2% to 1% by weight of the surface-modified absorbent polymer particles.

Typically, the absorbent polymer particles can have a selected particle size distribution. For example, the absorbent polymer particles may have a particle size distribution in the range from 45 μm to 4000 μm, more specifically from 45 μm to about 1000 μm, or from about 100 μm to about 850 μm, or from about 100 μm to about 600 μm. The particle size distribution of a material in particulate form can be determined as it is known in the art, for example by means of dry sieve analysis (EDANA 420.02 "Particle Size distribution). Optical methods, e.g. based on light scattering and image analysis techniques, can also be used.

Absorbent Core Profiled in the Transverse Dimension

Figure 5:
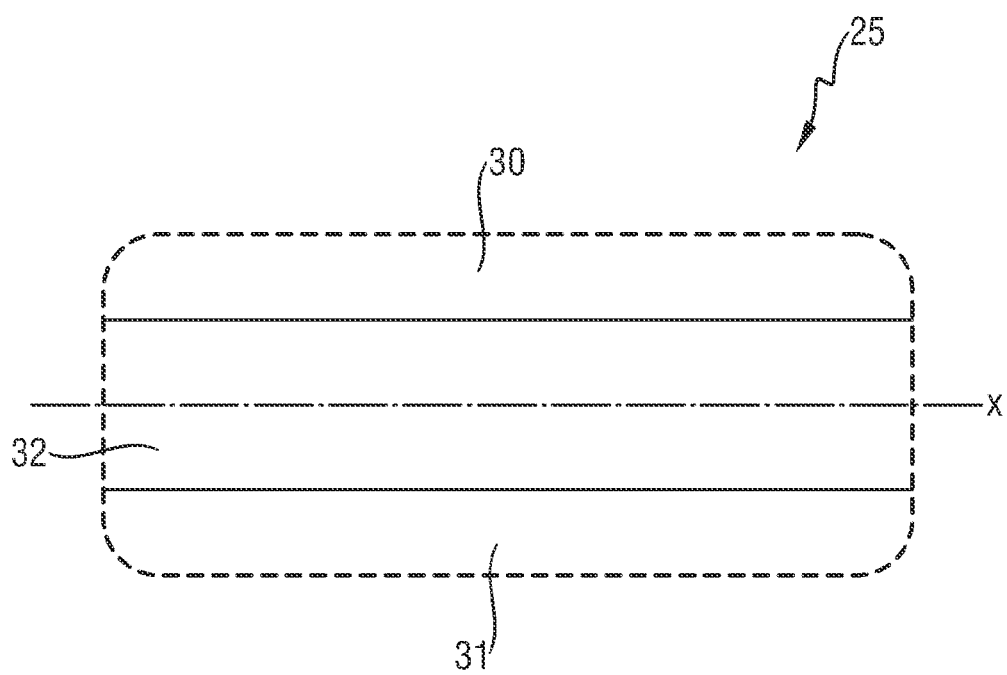
FIG. 5 is a top view of an absorbent layer.

In some embodiments, the amount of absorbent material, typically the amount of absorbent polymer material, in the absorbent layer or in at least one of the absorbent layers or in all the absorbent layers may vary along the transverse dimension of the absorbent layer. In some embodiments, as shown in FIG. 5, the absorbent layer 25 or at least one of the absorbent layers or all the absorbent layers may be divided in three absorbent zones, in which the amount of absorbent material, typically the amount of absorbent polymer material, per unit area of the absorbent layer varies from zone to zone. When divided in three zones, the absorbent layer has a first and second absorbent zone 30 and 31 spaced from one another and extending substantially parallel to the longitudinal axis of the absorbent layer and a central absorbent zone 32 between the first and second absorbent zone which extends substantially along the longitudinal axis (including said axis). In some embodiments, the absorbent material, typically the absorbent polymer material, present in the first and second absorbent zones of the absorbent layer may have a basis weight greater than the basis weight of the absorbent material present in the central absorbent zone of the absorbent layer. When the absorbent core according to these embodiments is subjected to a flush of liquid directed at the central absorbent zone, liquid that flows over and past the central absorbent zone contacts the side absorbent zones. The first and second absorbent zones have more absorbent polymer material and have greater capacity to absorb such liquid and deter flow of the liquid beyond the side absorbent zones to prevent leakage. In some embodiments, the basis weight of the absorbent material present in the first and second absorbent zones 30 and 31 of the absorbent layer may be lower than the basis weight of the absorbent material present in the central absorbent zone 32 of the absorbent layer. The absorbent layer may include any number of absorbent zones having varying basis weights of absorbent particulate polymer. Furthermore, in other embodiments, the absorbent material may be varied in different patterns such as by alternating areas of greater and lesser amounts of absorbent material per unit area of the absorbent layer.

In some embodiments as shown in FIG. 5, the areas of greater absorbent material basis weight are substantially parallel and continuous and the absorbent layer is substantially rectangular. In certain embodiments, areas of greater absorbent material basis weight may have other shapes such as curved or be intermittent, or both. FIG. 6A shows an embodiment comprising continuous areas of greater absorbent material basis weight 120b and 122b curved inwardly so as to form a concave pattern and adjacent areas of lower absorbent material basis weight 121b. FIG. 6B shows an embodiment comprising continuous areas of greater absorbent material basis weight 120c and 122c curved inwardly so as to form an hourglass pattern and a central area of lower absorbent material basis weight 121c. FIG. 6C shows an embodiment comprising continuous areas of greater absorbent material basis weight 120d and 122d curved outwardly so as to form a convex pattern and adjacent areas of lower absorbent material basis weight 121d. FIG. 6D shows an embodiment comprising substantially straight parallel areas of greater absorbent material basis weight 120e and 122e and adjacent areas of lower absorbent material basis weight 121e, the parallel areas of greater absorbent material basis weight 120e and 122e having a length shorter than that of the adjacent areas of lower absorbent material basis weight 121e. FIG. 6E shows an embodiment comprising substantially straight parallel intermittent areas of greater absorbent material basis weight 120f and 122f and adjacent areas of lower absorbent polymer material basis weight 121f.

Absorbent Core Profiled in the Longitudinal Dimension

Figure 7:
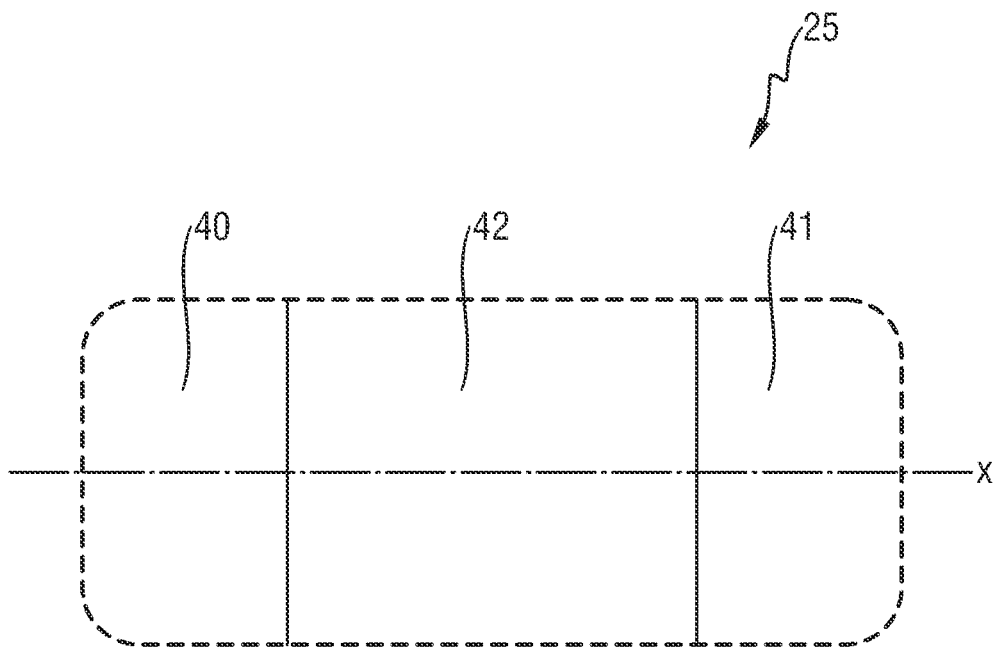
FIG. 7 is a top view of an absorbent layer.

In some embodiments, the amount of absorbent material in the absorbent layer or in at least one of the absorbent layers or in all the absorbent layers may vary along the longitudinal dimension of the absorbent layer. In some embodiments, such as shown in FIG. 7, the absorbent layer or at least one of the absorbent layers may be divided in three absorbent zones, in which the amount of absorbent material per unit area of the absorbent layer varies from zone to zone. When divided in three zones, the absorbent layer 25 has a first and second absorbent zone 40 and 41 spaced from one another and extending substantially perpendicular to the longitudinal axis of the absorbent layer, and a central absorbent zone 42 between the first and second end absorbent zones 40 and 41 which extends substantially along the transverse axis (including said axis). In some embodiments, the basis weight of the absorbent material in the first and second absorbent zones of the absorbent layer may be greater than in the central absorbent zone of the absorbent layer. These types of embodiments provide for a reduced bulk of the absorbent article in the crotch region and thus improve the fit of the article and thus the comfort for the wearer. When the absorbent core is subjected to a flush of liquid directed at the central absorbent zone, liquid that flows past the central absorbent zone encounters first and second absorbent zones which have greater capacity to absorb and hold such liquid. In some embodiments, the basis weight of the absorbent material in the first and second absorbent zones of the absorbent layer may be lower than in the central absorbent zone of the absorbent layer.

The absorbent layer may include any number of absorbent zones arranged in a variety of different patterns of varying absorbent material basis weights such as including a multitude of alternating absorbent zones of varying absorbent material basis weights.

The profiled absorbent core or absorbent structure may be obtained by any methods suitable for distributing absorbent material in patterns of varying absorbent material basis weights. Suitable methods for providing profiled absorbent cores are, for instance, disclosed in EP2328532A2 and EP 2328532A2.

The profiled absorbent layer of the absorbent structure may comprise absorbent material, such as absorbent polymer particles, distributed on the substrate layer such as to form as a continuous layer having zones of different basis weight, i.e. an uninterrupted layer of absorbent polymer material having zones of different basis weight. In some embodiments, it forms an uninterrupted layer of absorbent polymer particles having zones of different basis weight.

Alternatively, the profiled absorbent layer may comprise absorbent material, such as absorbent polymer particles, distributed on the substrate layer such as to form a discontinuous layer. In these embodiments, the absorbent polymer particles, and optionally cellulose, may be deposited on the substrate layer in clusters of particles, thus forming a discontinuous layer or an interrupted layer of absorbent polymer particles (and optionally cellulose). The clusters of absorbent polymer particles (and optionally cellulose) may have a variety of shape including, but not limited to, circular, oval, square, rectangular, triangular and the like which may provide for profiled absorbent particles distribution. Suitable methods for depositing particles in cluster of particles are disclosed in EP 1621167 A2, EP 1913914 A2, EP 2238953 A2, EP 2328532A2 and EP 2328532A2. The absorbent material may also be applied onto the substrate layer such that the absorbent material forms multiple stripes on the substrate layer spaced apart from each other to form gaps between neighboring stripes. In some embodiments, it forms stripes of absorbent polymer particles. The gaps between neighboring stripes are substantially free of absorbent material. "Substantially free of absorbent material" means that e.g. due to process-related reasons, a small, negligible amount of absorbent material may be present in the gaps, which does not contribute to the overall functionality. The term "substantially free of absorbent material" encompasses the term "free of absorbent material". The thermoplastic adhesive material may then be deposited to at least partially immobilize the absorbent material on the substrate layer. The thermoplastic adhesive material at least partially contacts the absorbent material and partially contacts the substrate layer.

In some embodiments, the absorbent core of the disposable diaper may comprise two or more absorbent structures as disclosed herein which are combined or superposed. Typically, the absorbent structures may be combined such that the thermoplastic adhesive material of the first absorbent structure directly contacts the thermoplastic adhesive material of the second absorbent structure. In some embodiments, a first and second absorbent structure may be combined such that when the absorbent material is distributed in stripes, the stripes of the first absorbent structure overlays the gaps formed in the second absorbent structure and the stripes of the second absorbent structure overlay the gaps of the first absorbent structure. In some embodiments, wherein the absorbent polymer particles are deposited on the substrate layer in clusters of particles, two absorbent structures are combined such that the resulting absorbent core comprises absorbent polymer particles substantially continuously distributed between the two substrate layers. "Substantially continuously distributed" as used herein indicates that the first substrate layer and second substrate layer are separated by a multiplicity of absorbent polymer particles. It is recognized that there may be minor incidental contact areas between the first substrate layer and second substrate layer within the absorbent particulate polymer material area (i.e. area between the two substrate layers). Incidental contact areas between the first substrate and second substrate may be intentional or unintentional (e.g. manufacturing artifacts) but do not form geometries such as pillows, pockets, tubes, quilted patterns and the like. The substrate layer of the two absorbent structure may be attached to each other at about the periphery to form an envelop, by an adhesive or any other means known in the art such as ultrasonic bonding, pressure bonding or thermal bonding.

Immobilization of the Absorbent Polymer Material by a Thermoplastic Adhesive Material The absorbent layer comprising the absorbent material is supported by a substrate layer and immobilized on said substrate layer by a thermoplastic adhesive material which provides immobilization in the dry and wet state.

The substrate layer of the absorbent structure may be any material capable to support the absorbent polymer particles. Typically, it is a web or sheet material, such as foam, film woven and/or nonwoven material. "Nonwoven material" as used herein refers to a manufactured web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise two steps: fiber laying onto a forming surface and fiber bonding. The fiber laying step may comprise spunlaying, meltblowing, carding, airlaying, wetlaying, coform and combinations thereof. The fiber bonding step may comprise hydroentanglement, cold calendering, hot calendering, through air thermal bonding, chemical bonding, needle punching, and combinations thereof. The nonwoven material may be a laminate. The laminate may comprise spunbond layer(s) (S), and/or meltblown layer(s) (M), and/or carded layer(s) (C). Suitable laminates include, but are not limited to, SS, SSS, SMS or SMMS. The nonwoven material may have a basis weight from about 5 to 100 g/m$^2$, or from about 10 to 40 g/m$^2$, or from about 10 to 30 g/m$^2$. Woven or nonwoven materials may comprise natural fibers or synthetic fibers or combinations thereof. Examples of natural fibers may include cellulosic natural fibers, such as fibers from hardwood sources, softwood sources, or other non-wood plants. The natural fibers may comprise cellulose, starch and combinations thereof. The synthetic fibers can be any material, such as, but not limited to, those selected from the group consisting of polyolefins (polypropylene and polypropylene copolymers, polyethylene and polyethylene copolymers), polyesters (e.g., polyethylene terephthalate), polyethers, polyamides, polyesteramides, polyvinylalcohols, polyhydroxyalkanoates, polysaccharides, and combinations thereof. Further, the synthetic fibers can be a single component (i.e. a single synthetic material or a mixture that makes up the entire fiber), bi-component (i.e. the fiber is divided into regions, the regions including two or more different synthetic materials or mixtures thereof and may include co-extruded fibers and core and sheath fibers) and combinations thereof. Bi-component fibers can be used as a component fiber of the nonwoven material, and/or they may be present to act as a binder for the other fibers present in the nonwoven material. Any or all of the fibers may be treated before, during, or after manufacture to change any desired properties of the fibers.

Thermoplastic adhesive materials suitable for immobilizing the absorbent layer which, generally, comprises an absorbent material consisting of absorbent polymer particles, typically combine good cohesion and good adhesion behavior. Good adhesion promotes good contact between the thermoplastic adhesive material and the absorbent material (e.g. absorbent polymer particles) and the substrate layer. Good cohesion reduces the likelihood that the adhesive breaks, in particular in response to external forces, and namely in response to strain. When the absorbent structure/core absorbs liquid, the absorbent polymer particles of the absorbent layer swell and subject the thermoplastic adhesive material to external forces.

Thermoplastic adhesive materials suitable for use in the present disclosure includes hot melt adhesives comprising at least a thermoplastic polymer in combination with a plasticizer and other thermoplastic diluents such as tackifying resins and additives such as antioxidants. Exemplary suitable hot melt adhesive materials are described in EP 1447067 A2. In some embodiments, the thermoplastic polymer has a molecular weight (Mw) of more than 10,000 and a glass transition temperature (Tg) below room temperature or $-6°$ C.$>$Tg$<16°$ C. In certain embodiments, the concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The thermoplastic adhesive material, typically a hot-melt adhesive material, is generally present in the form of fibres, i.e. the hot melt adhesive can be fiberized. In some embodiments, the thermoplastic adhesive material forms a fibrous network over the absorbent polymer particles. Typically, the fibres can have an average thickness from about 1 μm to about 100 μm, or from about 25 μm to about 75 μm, and an average length from about 5 mm to about 50 cm. In particular the layer of hot melt adhesive material can be provided such as to comprise a net-like structure.

An exemplary thermoplastic adhesive material may be a hot melt adhesive having a loss angle tan Delta at 60° C. of below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

It may be beneficial, e.g. for process reasons and/or performance reasons, that the thermoplastic adhesive material has a viscosity of between 800 and 4000 mPa·s, or from 1000 mPa·s or 1200 mPa·s or from 1600 mPa·s to 3200 mPa·s or to 3000 mPa·s or to 2800 mPa·s or to 2500 mPa·s, at 175° C., as measurable by ASTM D3236-88, using spindle 27, 20 pmp, 20 minutes preheating at the temperature, and stirring for 10 min.

The thermoplastic adhesive material may have a softening point of between 60° C. and 150° C., or between 75° C. and 135° C., or between 90° C. and 130° C., or between 100° C. and 115° C., as can be determined with ASTM E28-99 (Herzog method; using glycerine).

In one embodiment herein, the thermoplastic adhesive component may be hydrophilic, having a contact angle of less than 90°, or less than 80° or less than 75° or les than 70°, as measurable with ASTM D 5725-99.

The inventors have found that by modulating the amount of thermoplastic adhesive material applied over the profiled absorbent layer, the acquisition speed of the absorbent core could be improved. It was found that by providing a lower amount of thermoplastic adhesive material to immobilize the absorbent material, typically the absorbent polymer material, in one or more regions of the absorbent layer which comprise a lower amount of absorbent material, typically a lower amount of absorbent polymer material, an increase absorption speed could be achieved vs. providing a constant amount of thermoplastic adhesive material over the profiled absorbent layer. Indeed, it was found that providing a lower amount of thermoplastic adhesive material in one or more regions comprising a lower amount of absorbent material, typically a lower amount of absorbent polymer material, reduces the swelling restriction of the absorbent polymer material whilst maintaining efficient dry and wet immobilization of the absorbent polymer material.

Accordingly, in some embodiments where the absorbent core is profiled in its longitudinal dimension, the absorbent core comprises at least one transverse segment (out of the nine transverse segments) where the average basis weight of thermoplastic adhesive material and the average basis weight of absorbent material in the absorbent layer comprised by said segment are lower than the average basis weight of thermoplastic adhesive material and the average basis weight of absorbent material in the absorbent layer of one other transverse segment. Both the $APM_t BW_{av}$ and $TAM_t BW_{av}$ in at least one of the transverse segments of the absorbent core are lower than the $APM_t BW_{av}$ and $TAM_t BW_{av}$ in at least one other of said transverse segments. A transverse segment according to the above, i.e. a transverse segment which has both a lower $APM_t BW_{av}$ and a lower $TAM_t BW_{av}$ (relative to one other transverse segment) is referred herein as a "low basis weight transverse segment". In some embodiments, the absorbent material comprises more than 90% by weight, or more than 95% by weight or even comprises 100% by weight of absorbent polymer material. When the absorbent material consists of absorbent polymer material, the $APM_t BW_{av}$ is the average basis weight of absorbent polymer material in the absorbent layer of said segment. The average basis weight of thermoplastic adhesive material and the average basis weight of absorbent material of the absorbent layer per segment are determined according to methods known in the art. For each transverse segment, the $APM_t BW_{av}$ and the $TAM_t BW_{av}$ are determined. The transverse segment having the highest average basis weight of absorbent material within the nine segments is referred as the "reference segment". This "reference segment" has an $APM_t\ BW_{av\text{-}ref}$ and $TAM_t\ BW_{av\text{-}ref}$. There may be several reference segments, i.e. several segments having the same $APM_t\ BW_{av\text{-}ref}$ and the $TAM_t\ BW_{av\text{-}ref}$. Any transverse segment which has both a lower average basis weight of absorbent material and a lower average basis weight of thermoplastic polymer material than respectively the average basis weight of absorbent material and the average basis weight of thermoplastic polymer material of this "reference segment" ($APM_t\ BW_{av\text{-}x} < APMt\ BW_{av\text{-}ref}$ and $TAM_t\ BW_{av\text{-}x} < TAM_t\ BW_{av\text{-}ref}$) is referred as a "low basis weight transverse segment".

The absorbent core may comprise more than one "low basis weight transverse segment". For in instance, the absorbent core may comprise two, three, four, five or six "low basis weight transverse segments". When the absorbent core comprises more than one "low basis weight transverse segment", such as two, three, four, five or six, these "low basis weight transverse segments" may be adjacent to each others or may be separated.

Figure 8:
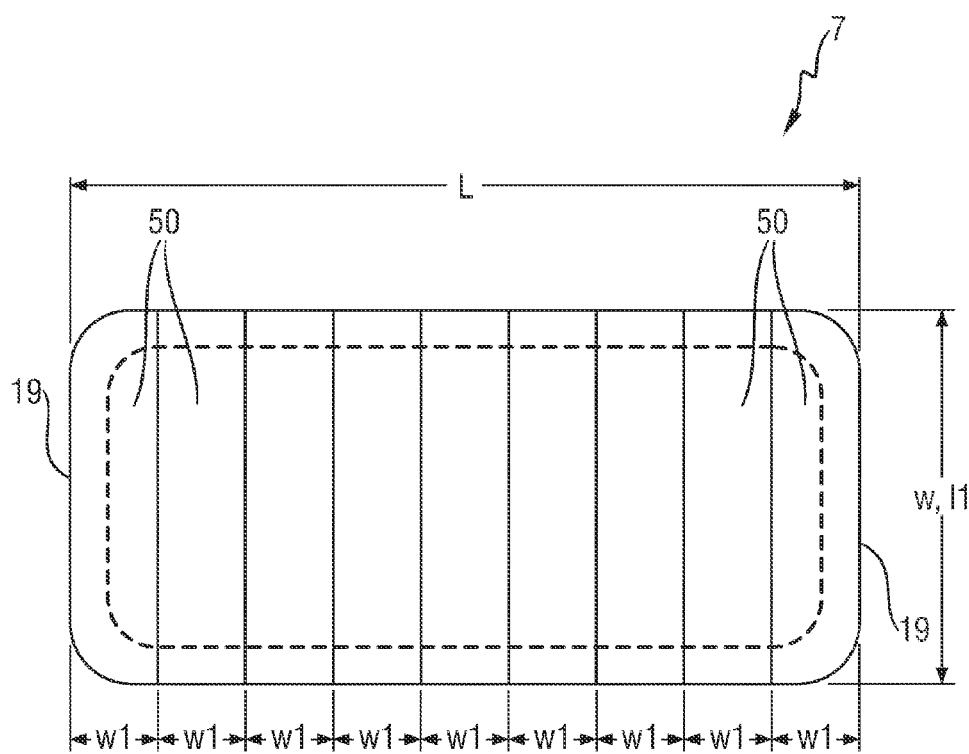
FIG. 8 is a top view of an absorbent core.

In some embodiments, such as shown in FIG. 8, the absorbent core may comprise four low basis weight transverse segments 50. Two of them are contiguous with one the two being adjacent to one transverse edge 19 of the absorbent core. The other two low basis weight transverse segments are also contiguous with one of the two being adjacent to the opposite transverse edge 19 of the absorbent core. The four "low basis weight segments" 50 may have the same $APM_t\ BW_{av}$ and $TAM_t\ BW_{av}$ or they may have different $APM_t\ BW_{av}$ and/or $TAM_t\ BW_{av}$. The five other transverse segments have a same $TAM_t\ BW_{av}$ (i.e. which is higher than the $TAM_t\ BW_{av}$ of the "low basis weight transverse segments") but may have a different $APM_t\ BW_{av}$ (which may be higher or lower than the $APM_t\ BW_{av}$ of the "low basis weight transverse segments" provided at least one of said five segments has an $APM_t\ BW_{av}$ higher than the $APM_t\ BW_{av}$ of the "low basis weight segments"). Typically, the five other transverse segments have a same $TAM_t\ BW_{av}$ (i.e. which is higher than the $TAM_t\ BW_{av}$ of the low basis weight transverse segments) but all have an $APM_t\ BW_{av}$ higher than the $APM_t\ BW_{av}$ of the low basis weight transverse segments. In these embodiments, most of the absorbent capacity is typically provided around the crotch region of the absorbent core as defined above, i.e. the basis weight of absorbent material is higher in the crotch region and neighboring regions vs. regions oriented close to the front waist region and back waist of the absorbent core. In some other embodiments, the four "low basis weight transverse segments" may be contiguous and distributed at least in the crotch region. In these embodiments, the crotch region may comprise a lower amount of absorbent material and a lower amount of thermoplastic adhesive material versus the adjacent regions which reduce the bulk of the article, especially when loaded with body fluids, in the crotch region and also reduce the stiffness of the disposable article in said crotch region. The comfort of the wearer is thereby improved.

Figure 9:
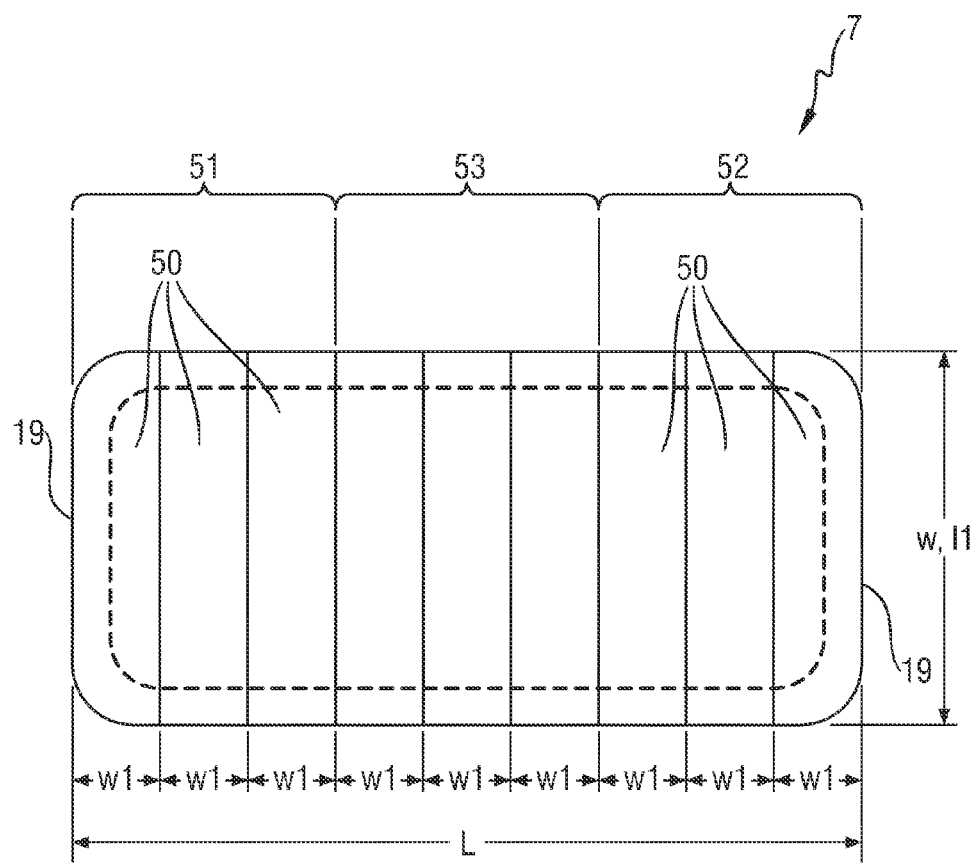
FIG. 9 is a top view of an absorbent core.

In some embodiments, the absorbent core may comprise six "low basis weight transverse segments". In an exemplary embodiment, such as shown in FIG. 9, three of said low basis weight transverse segments 50 may be contiguous with one of them being adjacent to one transverse edge 19 of the absorbent core. The three other "low basis weight transverse segments" 50 may also be contiguous with one of them being adjacent to the opposite transverse edge 19 of the absorbent core. The end portion of the absorbent core which comprises three of the low basis weight transverse segments 50 (⅓ of the length of the absorbent core) is the front region 51 of the absorbent core. The end portion of the absorbent core which comprises the three other "low basis weight transverse segments" (⅓ of the length of the absorbent core) is the back region 52 of the absorbent core. The intermediate portion of the absorbent core which does not comprise any "low basis weight transverse segments" is the crotch region 53. In these embodiments, the absorbent core comprises a lower basis weight of thermoplastic adhesive material in the regions comprising a lower amount of absorbent material, namely the front and back regions, the crotch region comprising most of the absorbent capacity. The six "low basis weight segments" 50 may have the same $APM_t\ BW_{av}$ and $TAM_t\ BW_{av}$ or they may have different $APM_t\ BW_{av}$ and/or $TAM_t\ BW_{av}$. The three other transverse segments have a same $TAM_t\ BW_{av}$ (i.e. which is higher than the $TAM_t\ BW_{av}$ of the low basis weight transverse segments) but may have a different $APM_t\ BW_{av}$ (which may be higher or lower than the $APM_t\ BW_{av}$ of the low basis weight transverse segment provided at least one of said three segments has an $APM_t\ BW_{av}$ higher than the $APM_t\ BW_{av}$ of the low basis weight segments). Typically, the three other transverse segments have a same $TAM_t\ BW_{av}$ (i.e. which is higher than the $TAM_t\ BW_{av}$ of the low basis weight transverse segments) and all have an $APM_t\ BW_{av}$ higher than the $APM_t\ BW_{av}$ of the low basis weight transverse segments.

In some embodiments, the one or more "low basis weight transverse segments" are distributed in the crotch region and neighboring regions of the absorbent core. In these embodiments, the crotch region of the absorbent core comprises a lower amount of absorbent material vs. the back and front region of the absorbent core. In some embodiments, the absorbent core comprises three "low basis weight transverse segments" which are distributed in the crotch region of the absorbent core.

In some embodiments, the absorbent core may comprise three low basis weight transverse segments. The three low basis weight segments may be contiguous. In some embodiments, the three low basis weight segments may be in the back region of the absorbent core (the back region of the absorbent core being as defined above). In these embodiments, the absorbent core may be profiled such that it comprises higher basis weight of thermoplastic adhesive material in the front and crotch region vs. the back region. A lower basis weight of thermoplastic adhesive material is then applied in the back region of the absorbent core.

Alternatively, in some embodiments where the absorbent core is profiled in its transverse dimension, the absorbent core comprises at least one longitudinal segment (out of the six longitudinal segments) wherein the average basis weight of thermoplastic adhesive material and the average basis weight of absorbent material in the absorbent layer comprised by said segment are lower than the average basis weight of thermoplastic adhesive material and the average basis weight of absorbent material in the absorbent layer of one other longitudinal segment. Both the $APM_1\ BW_{av}$ and $TAM_1\ BW_{av}$ in at least one of said longitudinal segments of the absorbent core are lower than the $APM_1\ BW_{av}$ and $TAM_1\ BW_{av}$ in at least one other of said transverse segments. A longitudinal segment according to the above, i.e. a longitudinal segment which has both a lower $APM_1\ BW_{av}$ and a lower $TAM_1\ BW_{av}$ (relative to one other longitudinal segment) is referred herein as a "low basis weight longitudinal segment". In some embodiments, the absorbent material comprises more than 90% by weight, or more than 95% by weight or even comprises 100% by weight of absorbent polymer material. When the absorbent material consists of absorbent polymer material, the $APM_1\ BW_{av}$ is the average basis weight of absorbent polymer material in the absorbent layer of said segment. The average basis weight of thermoplastic adhesive material and the average basis weight of absorbent material of the absorbent layer per segment are determined according to methods known in the art. For each longitudinal segment of the absorbent core, the $APM_1\ BW_{av}$ and the $TAM_1\ BW_{av}$ are determined. The longitudinal segment having the highest average basis weight of absorbent material within the six segments is referred as the "reference segment". This "reference segment" has an $APM_1\ BW_{av\text{-}ref}$ and $TAM_1\ BW_{av\text{-}ref}$. There may be several reference segments, i.e. several segments having the same $APM_1\ BW_{av\text{-}ref}$ and $TAM_1\ BW_{av\text{-}ref}$. Any longitudinal segment which has both a lower average basis weight of absorbent material and a lower average basis weight of thermoplastic polymer material than respectively the average basis weight of absorbent material and the average basis weight of thermoplastic polymer material of this "reference segment" ($APM_1\ BW_{av\text{-}x}\ APM_1\ BW_{av\text{-}ref}$ and $TAM_1\ BW_{av\text{-}x} < TAM_1\ BW_{av\text{-}ref}$) is referred as a "low basis weight longitudinal segment".

In some embodiments, the absorbent core may comprise one low basis weight longitudinal segment. The low basis weight longitudinal segment may extends along the longitudinal axis (and including said axis) of the absorbent core.

In some embodiments, the absorbent core comprises two, three or four of said low basis weight longitudinal segments. When the absorbent core comprises more than "one low basis weight longitudinal segment", such as two, three, four "low basis weight longitudinal segments", all the "low basis weight longitudinal segments" may be contiguous or only some of them may be contiguous.

In some embodiments, the absorbent core may comprise two "low basis weight longitudinal segments" extending respectively along the longitudinal edges of the absorbent core.

Figure 10:
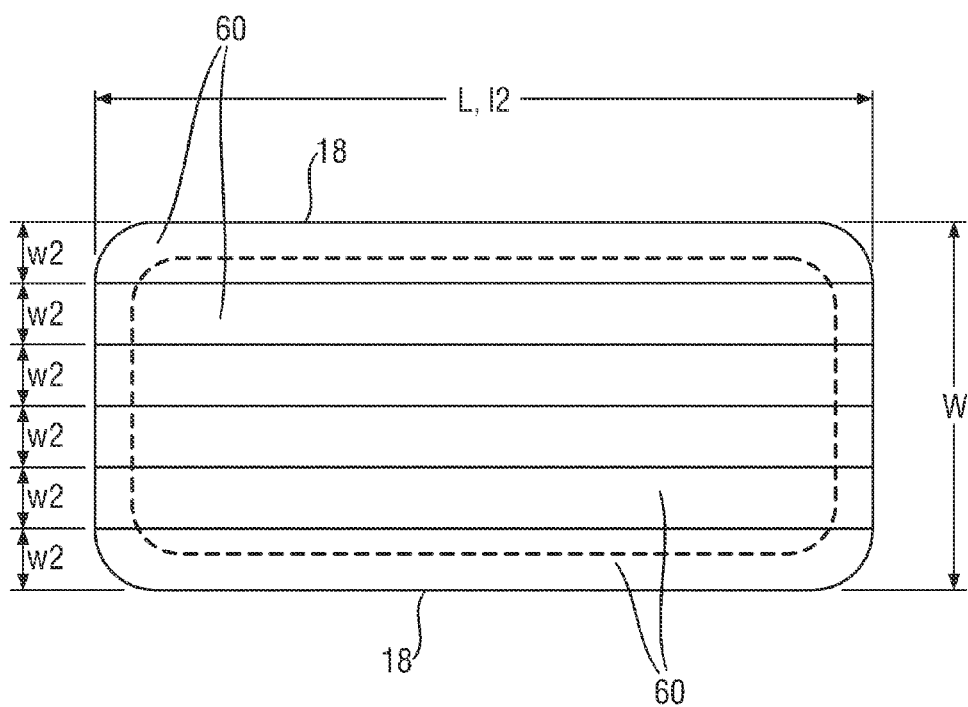
FIG. 10 is a top view of an absorbent core.

In some embodiments, such as shown in FIG. 10, the absorbent core may comprise four "low basis weight longitudinal segments" 60. Two of them 60 are contiguous with one of them being adjacent to one longitudinal edge 26 of the absorbent core. The two others 60 are also contiguous with one of them being adjacent to the opposite longitudinal edge 26 of the absorbent core. The four low basis weight segments 60 may have the same $APM_1\ BW_{av}$ and $TAM_1\ BW_{av}$ or they may have different $APM_1\ BW_{av}$ and/or $TAM_1\ BW_{av}$. The two other longitudinal segments have a same $TAM_1\ BW_{av}$ (i.e. which is higher than the $TAM_1\ BW_{av}$ of the low basis weight longitudinal segments) but may have a different $APM_1\ BW_{av}$ (which may be higher or lower than the $APM_1\ BW_{av}$ of the low basis weight longitudinal segments provided at least one of said two segments has an $APM_1\ BW_{av}$ higher than the $APM_1\ BW_{av}$ of the low basis weight segments). Typically, these two longitudinal segments have a higher average basis weight of absorbent material than the four low basis weight longitudinal segments.

The average basis weight of thermoplastic adhesive material in one of said low basis weight transverse or longitudinal segments or in all of them may be at least 10%, or at least 20%, or at least 30%, or at least 50% lower relative to the average basis weight of thermoplastic adhesive material in the reference segment (the reference segment being determined as indicated above).

The average basis weight of absorbent material in one of said low basis weight transverse or longitudinal segments or in all of them may be at least 10%, or at least 20%, or at least 30%, or at least 50% lower relative to the average basis weight of absorbent material in the reference segment (the reference segment being determined as indicated above).

In some embodiments, the average basis weight of thermoplastic adhesive material and average basis weight of absorbent material of said low basis weight transverse or longitudinal segments may be at least 20% lower, such as 20% or 25% or 30% or 50% lower, than respectively the average basis weight of thermoplastic adhesive material and average basis weight of absorbent material in the reference segment (the reference segment being determined as indicated above).

In some embodiments, the average basis weight of thermoplastic adhesive material of said low basis weight transverse or longitudinal segments may be from 50% to 65% lower than the average basis weight of thermoplastic adhesive material in the reference segment when the average basis weight of absorbent material of said low basis weight transverse or longitudinal segments is from 25% to 45% lower than in the reference segment (the reference segment being determined as indicated above).

In some embodiments, the average basis weight of absorbent material (e.g. absorbent polymer particles) in the one or more "low basis weight longitudinal" segment or one or more "low basis weight transverse segment" may be from 50 gsm to 350 gsm, or from 75 gsm to 300 gsm or from 80 gsm to 275 gsm, the average basis weight of absorbent material in the other segments being of at least 350 gsm and up 1500 gsm, or up to 1000 gsm.

In some embodiments, the average basis weight of thermoplastic adhesive material in the one or more "low basis weight longitudinal" segment or one or more "low basis weight transverse segment" may be from 0.5 gsm to 4 gsm, or from 1 gsm to 3 gsm, the average basis weight of thermoplastic adhesive material in the other segments being of at least 5 gsm and up 30 gsm.

Method for Making Absorbent Cores

The profiled absorbent core can be made by any suitable methods available in the art, such as disclosed in EP2328532A2 and EP 2328532A2.

The method for making the absorbent core of the present disclosure comprises the steps of:
 (a) forming an absorbent structure by:
   (a) providing a substrate layer;
   (b) forming a profiled absorbent layer by depositing an absorbent material comprising absorbent polymer material on said substrate layer to create zones of different absorbent material basis weight;
   (c) applying thermoplastic adhesive material on one or more first zones of the absorbent layer at a first basis weight;
   (d) applying thermoplastic adhesive material on one or more second zones of the absorbent layer at a second basis weight, said second zones being different from said first zones;
   (e) optionally, applying thermoplastic adhesive material on one or more third zones of the absorbent layer a third basis weight, said third zones being different from said first and second zones;
 (b) optionally, repeating steps (a) to (e) and combining the two absorbent structures such that the thermoplastic adhesive material of the first absorbent structure contacts the thermoplastic adhesive material of the second absorbent structure.

A printing system may be used for making an absorbent core in accordance with the present disclosure. The system may comprise a printing unit for forming the absorbent structure. When the absorbent core is a laminate, the system may comprise a first printing unit for forming the first absorbent structure of the absorbent core and a second printing unit for forming the second absorbent structure of the absorbent core.

A printing unit may comprise a rotatable support roll for receiving the substrate layer, a hopper for holding absorbent polymer material, a printing roll for transferring the absorbent polymer material to the substrate layer, and thermoplastic adhesive material applicators for applying the thermoplastic adhesive material to the substrate and the absorbent polymer material thereon in accordance with the present disclosure.

The printing roll comprises a rotatable drum and a plurality of absorbent polymer material reservoirs in a peripheral surface of the drum. The reservoirs may have a variety of shapes, including cylindrical, conical, or any other shape. The first printing roll is designed to produce a profiled absorbent core. This effect may be achieved by having a corresponding set of reservoirs which are relatively deep and a second set of reservoirs which are relatively shallow, such that the deeper reservoirs carry more absorbent polymer material and deliver more absorbent polymer material to the targeted zone and the more shallow reservoirs hold less particulate polymer material and deliver less absorbent polymer material to a target zone of the absorbent core. Other methods of delivering a varying profile of absorbent polymer basis weights to the absorbent core includes, but is not limited to, applying a higher vacuum in sections of the first and second rotatable support rolls where more absorbent polymer material is desired or, when the absorbent polymer material is delivered to the substrate layer pneumatically, such as when combining cellulosic fibers with absorbent polymer material, directing the air stream carrying the absorbent polymer material and cellulosic fibers to areas of the absorbent core substrate where a higher basis weight of absorbent polymer material is desired.

In operation, the printing system receives the substrate layer into the printing unit. A vacuum within the support roll draws the substrate layer against the vertical support grid and holds the substrate layer against the support roll. This presents an uneven surface on the substrate layer. Due to gravity, or by using the vacuum means, the substrate layer will follow the contours of the uneven surface and thereby the substrate layer will assume a mountain and valley shape. The absorbent particulate polymer material may accumulate in the valleys presented by the substrate layer. The support roll then carries the substrate layer past the rotating printing roll which transfers the absorbent polymer material from the hopper to the substrate layer in the grid pattern. A vacuum in the printing roll may hold the absorbent polymer material in the reservoirs until time to deliver the absorbent polymer material to the substrate layer. The vacuum may then be released or air flow through the air passages may be reversed to eject the absorbent polymer material from the reservoirs and onto the substrate layer. The absorbent polymer material may accumulate in the valleys presented by the substrate layer. The support roll then carries the printed substrate layer past the thermoplastic adhesive material applicators which apply different basis weight of thermoplastic adhesive material to cover the absorbent polymer material on the first substrate in accordance with the present disclosure.

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for disposable absorbent articles comprising one or more absorbent structures, said absorbent structure comprising a substrate layer and an absorbent layer, said absorbent layer comprising an absorbent material supported by, and immobilized on said substrate layer by a thermoplastic adhesive material;

wherein said absorbent core has a longitudinal dimension having a length and a transverse dimension having a width and consists of nine transverse segments in its longitudinal dimension and of six longitudinal segments in its transverse dimension;

wherein each of the transverse segments have a length which is equal to the width of the absorbent core and a width which correspond to ⅑ of the length of the absorbent core; wherein each of the longitudinal segments have a length which is equal to the length of the absorbent core and a width which correspond to ⅙ of the width of the absorbent core;

wherein in each of said transverse segments, the absorbent layer has an average basis weight of absorbent material ($APM_t\ BW_{av}$) and an average basis weight of thermoplastic adhesive material ($TAM_t\ BW_{av}$) immobilizing said absorbent material;

wherein in each of said longitudinal segments, the absorbent layer has an average basis weight of absorbent material ($APM_l\ BW_{av}$) and an average basis weight of thermoplastic adhesive material ($TAM_l\ BW_{av}$) immobilizing said absorbent material;

wherein said absorbent core comprises six transverse segments wherein the $APM_t\ BW_{av}$ and $TAM_t\ BW_{av}$ of the absorbent layer are lower relative to the $APM_t\ BW_{av}$ and $TAM_t\ BW_{av}$ of the absorbent layer in at least one other of said transverse segments; and wherein the $APM_l\ BW_{av}$ and $TAM_l\ BW_{av}$ of the absorbent layer in at least one of said longitudinal segments are lower relative to the $APM_l\ BW_{av}$ and $TAM_l\ BW_{av}$ of the absorbent layer in at least one other of said longitudinal segments.

2. The absorbent core of claim 1, wherein said absorbent material comprises at least 95% by weight of absorbent polymer material.

3. The absorbent core of claim 1, wherein said absorbent core has a pair of opposing transverse edges and a pair of opposing longitudinal edges, and wherein three of said six transverse segments wherein the $APM_t\ BW_{av}$ and $TAM_t\ BW_{av}$ of the absorbent layer are lower relative to the $APM_t\ BW_{av}$ and $TAM_t\ BW_{av}$ of the absorbent layer in at least one other of said transverse segments are adjacent to each other and to an opposite transverse edge of said absorbent core and three of said six transverse segments wherein the $APM_t\ BW_{av}$ and $TAM_t\ BW_{av}$ of the absorbent layer are lower relative to the $APM_t\ BW_{av}$ and $TAM_t\ BW_{av}$ of the absorbent layer in at least one other of said transverse segments are adjacent to each other and to the opposite transverse edge of said absorbent core.

4. The absorbent core of claim 1, wherein said absorbent core comprises two longitudinal segments wherein the $APM_1\ BW_{av}$ and $TAM_1\ BW_{av}$ of the absorbent layer are lower relative to the $APM_1\ BW_{av}$ and $TAM_1\ BW_{av}$ of the absorbent layer in at least one other of said longitudinal segment.

5. The absorbent core of claim 1, wherein said absorbent core comprises a front region, a crotch region and a back region arranged sequentially in said longitudinal dimension and wherein said absorbent core comprises three transverse segments in said crotch region wherein the $APM_t\ BW_{av}$ and $TAM_t\ BW_{av}$ of the absorbent layer are lower than the $APM_t\ BW_{av}$ and $TAM_t\ BW_{av}$ of the absorbent layer in at least one other of said transverse segments.

6. The absorbent core of claim 1, wherein said absorbent core comprises three longitudinal segments wherein the $APM_1\ BW_{av}$ and $TAM_1\ BW_{av}$ of the absorbent layer are lower than the $APM_1\ BW_{av}$ and $TAM_1\ BW_{av}$ of the absorbent layer in at least one other of said longitudinal segment, three of said six longitudinal segments being contiguous and adjacent to one longitudinal edge of said absorbent core and three of said six longitudinal segments being contiguous and adjacent to the other longitudinal edge of said absorbent core.

7. The absorbent core of claim 1, wherein $TAM_t\ BW_{av}$ or $TAM_1\ BW_{av}$ is at least 20% lower than the average basis weight of the at least one segment.

8. The absorbent core of claim 1, wherein $TAM_t\ BW_{av}$ or $TAM_1\ BW_{av}$ is at least 40% lower than the average basis weight of the at least one segment.

9. The absorbent core of claim 1, wherein $APM_t\ BW_{av}$ or $APM_1\ BW_{av}$ is at least 20% lower than the average basis weight of the at least one segment.

10. The absorbent core of claim 1, further comprising two absorbent structures forming a laminate of absorbent structures with two absorbent layers wherein the $APM_t\ BW_{av}$ and $TAM_t\ BW_{av}$ of said absorbent layers in at least one of said transverse segments are lower relative to the $APM_t\ BW_{av}$ and $TAM_t\ BW_{av}$ of the absorbent layers in at least one other of said transverse segments.

11. The absorbent core of claim 1, wherein the $APM_t\ BW_{av}$ or $APM_1\ BW_{av}$ of the at least one of the transverse or longitudinal segments, respectively, is at least from 50% to 65% lower than the at least one of the other transverse or longitudinal segments when the $TAM_t\ BW_{av}$ or $TAM_1\ BW_{av}$ of the at least one of the transverse segments or longitudinal segments, respectively, is from 25% to 45% lower than the at least one of the other transverse or longitudinal segments.

12. A disposable absorbent article having a longitudinal axis extending from a first end to a second end and comprising a topsheet and a backsheet and an absorbent core according to claim 1 between the topsheet and the backsheet.

13. The disposable absorbent article of claim 12, wherein said article is a diaper.

14. A method for making an absorbent core of claim 1 which comprises the steps of forming an absorbent structure by:
(a) providing a substrate layer;
(b) forming a profiled absorbent layer by depositing an absorbent material comprising absorbent polymer material on said substrate layer to create zones of different absorbent material basis weight;
(c) applying thermoplastic adhesive material on one or more first zones of the absorbent layer at a first basis weight;
(d) applying thermoplastic adhesive material on one or more second zones of the absorbent layer at a second basis weight, said second zones being different from said first zones; and
(e) optionally, applying thermoplastic adhesive material on one or more third zones of the absorbent layer a third basis weight, said third zones being different from said first and second zones.

* * * * *